US008841498B2

(12) United States Patent
Birke et al.

(10) Patent No.: US 8,841,498 B2
(45) Date of Patent: Sep. 23, 2014

(54) CATALYST FOR THE HYDROGENATION OF UNSATURATED HYDROCARBONS AND PROCESS FOR ITS PREPARATION

(71) Applicant: Shell Oil Company, Houston, TX (US)

(72) Inventors: Peter Birke, Leuna (DE); Reinhard Geyer, Leuna (DE); Jurgen Hunold, Leuna (DE); Peter Kraak, Leuna (DE); Rainer Schoedel, Leuna (DE)

(73) Assignee: Shell Oil Company, Houston, TX (US)

( * ) Notice: Subject to any disclaimer, the term of this patent is extended or adjusted under 35 U.S.C. 154(b) by 0 days.

(21) Appl. No.: 13/944,968

(22) Filed: Jul. 18, 2013

(65) Prior Publication Data

US 2013/0303812 A1 Nov. 14, 2013

Related U.S. Application Data

(62) Division of application No. 12/682,894, filed as application No. PCT/EP2008/064078 on Oct. 10, 2008, now Pat. No. 8,518,851.

(30) Foreign Application Priority Data

Oct. 19, 2007 (EP) .................................. 07118871

(51) Int. Cl.
| | |
|---|---|
| C07C 5/10 | (2006.01) |
| B01J 21/00 | (2006.01) |
| C10G 45/00 | (2006.01) |
| B01J 23/755 | (2006.01) |
| C10G 45/08 | (2006.01) |
| B01J 37/03 | (2006.01) |
| C10G 45/48 | (2006.01) |
| B01J 23/78 | (2006.01) |
| B01J 23/86 | (2006.01) |
| B01J 23/80 | (2006.01) |
| B01J 35/10 | (2006.01) |
| B01J 37/18 | (2006.01) |
| B01J 37/00 | (2006.01) |
| B01J 35/00 | (2006.01) |
| B01J 37/14 | (2006.01) |
| B01J 21/08 | (2006.01) |

(52) U.S. Cl.
CPC ............ *B01J 23/866* (2013.01); *B01J 35/1042* (2013.01); *C07C 2521/06* (2013.01); *C10G 45/00* (2013.01); *B01J 37/18* (2013.01); *B01J 37/0036* (2013.01); *B01J 23/755* (2013.01); *C07C 2523/755* (2013.01); *C07C 5/10* (2013.01); *C10G 45/08* (2013.01); *B01J 35/006* (2013.01); *B01J 37/03* (2013.01); *B01J 37/14* (2013.01); *C07C 2521/08* (2013.01); *B01J 35/108* (2013.01); *C10G 45/48* (2013.01); *B01J 23/78* (2013.01); *B01J 21/08* (2013.01); *B01J 23/80* (2013.01)
USPC ............ 585/270; 502/242; 502/250; 502/251; 502/252; 502/253; 502/257; 502/259; 502/263

(58) Field of Classification Search
USPC ......... 502/242, 250–253, 256, 257, 259, 263; 585/270
See application file for complete search history.

(56) References Cited

U.S. PATENT DOCUMENTS

| | | | | |
|---|---|---|---|---|
| 3,558,471 | A * | 1/1971 | Kittrell | 208/59 |
| 3,993,597 | A * | 11/1976 | Stiles | 502/2 |
| 4,595,667 | A * | 6/1986 | Takase et al. | 502/63 |
| 5,028,665 | A | 7/1991 | Hecul | |
| 5,149,893 | A | 9/1992 | King et al. | |
| 5,407,886 | A * | 4/1995 | Schneider et al. | 502/244 |
| 5,478,791 | A * | 12/1995 | Baldauf et al. | 502/337 |
| 5,612,422 | A | 3/1997 | Hucul et al. | |
| 6,376,622 | B1 | 4/2002 | Hucul | |
| 7,348,463 | B2 * | 3/2008 | Ryu | 585/270 |
| 7,528,092 | B2 * | 5/2009 | Berben et al. | 502/251 |
| 7,915,196 | B2 * | 3/2011 | Parent et al. | 502/335 |
| 8,207,083 | B2 * | 6/2012 | Berben et al. | 502/252 |
| 2007/0036713 | A1 * | 2/2007 | Kobayashi et al. | 423/652 |
| 2007/0117714 | A1 | 5/2007 | Geyer et al. | |
| 2008/0139383 | A1 * | 6/2008 | Ryu | 502/327 |

FOREIGN PATENT DOCUMENTS

| | | |
|---|---|---|
| DE | 19909176 | 9/2000 |
| DE | 19909177 | 9/2000 |
| EP | 0290100 | 11/1988 |
| EP | 0398446 | 11/1990 |
| EP | 0974637 | 1/2000 |
| EP | 1262234 | 12/2002 |
| EP | 1331033 | 7/2003 |
| JP | 03076706 | 4/1991 |
| WO | 0136093 | 5/2001 |
| WO | 2004035204 | 4/2004 |
| WO | 2006070007 | 7/2006 |

* cited by examiner

*Primary Examiner* — Cam N. Nguyen

(57) ABSTRACT

The present invention relates to a catalyst for the hydrogenation of unsaturated hydrocarbons, in particular aromatics with a broad molecular weight range, a process for the production thereof and a process for hydrogenating unsaturated hydrocarbons.

13 Claims, No Drawings

CATALYST FOR THE HYDROGENATION OF UNSATURATED HYDROCARBONS AND PROCESS FOR ITS PREPARATION

CROSS REFERENCE TO RELATED APPLICATIONS

This application is a divisional of U.S. application Ser. No. 12/682,894, filed on 17 Oct. 2008, which claims priority to PCT/EP2008/064078, filed 10 Oct. 2008, which claims priority to European patent application 07118871.8, filed 19 Oct. 2007.

DESCRIPTION

The present invention relates to a catalyst for the hydrogenation of unsaturated hydrocarbons, in particular aromatics with a broad molecular weight range, a process for the production thereof and a process for hydrogenating unsaturated hydrocarbons.

The catalytic hydrogenation of aromatics is well known. EP 0 290 100 discloses shaped nickel-theta $Al_2O_3$ catalysts containing 5 to 40 weight-% nickel for the hydrogenation of aromatics-containing hydrocarbons. The catalyst support used has practically no pores smaller than 2.0 nm. The mean pore radius of the catalysts lies in the range 7.4 to 10.3 nm. The nickel impregnation is effected from ammoniacal solution.

In EP 0 398 446, a catalyst system for the hydrogenation of aromatics in solvents and white oil with high resistance to sulphur compounds is disclosed. The catalysts contain separately on a support a hydrogenation component and a metal oxide. As metals, Cu, Ni, Pt, Pd, Rh, Ru, Co or mixtures of these metals and as a metal oxide component the oxides of Ag, La, Sb, V, Ni, Bi, Cd, Pb, Sn, V, Ca, Sr, Ba, Co, Cu, W, Zn, Mo, Mn, Fe or mixtures of these oxides are disclosed. The catalyst support can consist of $Al_2O_3$, $SiO_2$, $Al_2O_3.SiO_2$, $TiO_2$, $ZrO_2$ and MgO.

Still greater sulphur resistance is attained according to EP 0 974 637 through a combination of a noble metal-containing supported catalyst, a metal oxide-containing and a Ni—$SiO_2$ catalyst. Thus, for example, a Pt/Pd supported catalyst is provided at the reactor head, and beneath this is a mixture of ZnO extrudates and Ni—$SiO_2$ extrudates.

JP 3076706 describes the hydrogenation of unsaturated polymers with a Pd supported catalyst, wherein $SiO_2$ supports with a pore diameter of 20 to 50 nm are used. In this process, however, the catalyst consumption is very high.

U.S. Pat. No. 5,028,665 discloses a metal supported catalyst for the hydrogenation of unsaturated polymers the support thereof predominantly has pores of pore diameters >45 nm. The catalysts hydrogenate 90 to 100% of the olefinic compounds, but only <25% of the aromatics. Pd, Pt and Rh are described as hydrogenation-active metals.

In U.S. Pat. No. 5,612,422, a metal-$SiO_2$ supported catalyst is described for the hydrogenation of polymers with mean molecular weights of 100 000, the support thereof has a pore volume which is to at least 98% constituted of pores with pore diameters >60 nm. Pt and Rh are mentioned as preferred hydrogenation-active metals.

For the hydrogenation of resins, a catalyst is disclosed in WO 01/36093 A1 which contains 45 to 85% Ni on $SiO_2$ (14 to 45 weight-%), $Al_2O_3$ (1 to 15 weight-%) and 0.25 to 4 weight-% Fe and has a pore volume of at least 0.35 ml/g in the pore diameter range from 2 to 60 nm.

In EP 1 262 234, catalysts for the hydrogenation of aromatics with a low tendency to cracking are described, which contain 0.1 to 2.0 weight-% of a noble metal of the $8^{th}$ subgroup on a $SiO_2$—MgO support with a MgO content of 25 to 50 weight-%. The pore volume with pore diameters >4.0 nm should lie in the range from 0.3 to 0.6 ml/g and that with pore diameters from 0.7 to 2 nm at 0.2 to 0.3 ml/g. The pore volume with pore radii of at least 200 nm should not be greater than 0.05 ml/g.

U.S. Pat. No. 6,376,622 discloses metal-$SiO_2$ supported catalysts for the hydrogenation of olefins and aromatics in polymers with mean molecular weights from 40 000 to 120 000, wherein the support used has surface areas from 30 to 120 $m^2/g$, 95% of the pore volume is formed by pores with pore diameters of 30 to 100 nm and the proportion of the pore volume with pore diameters <20 nm is less than 4%. The hydrogenating component is Ni, Co, Rh, Ru, Pd, Pt or a combination thereof.

In U.S. Pat. No. 5,149,893, a Ni- or Co-calcium aluminate catalyst for the hydrogenation of benzene is disclosed.

These catalyst systems are either preferred for the hydrogenation of aromatics with low molecular weights or predominantly suitable for the hydrogenation of higher molecular weight aromatic compounds.

EP 1 331 033 discloses a process for the production of spherical metal support catalysts useful for the hydrogenation of aromatic substances.

DE 19909177 discloses supported nickel catalysts, preferably having a high zirconium content, for the hydrogenation of functional groups of organic compounds.

The technical problem underlying the present invention is to provide a catalyst system with a high catalytic activity which is particularly suitable for the hydrogenation of both higher and lower molecular weight aromatic compounds.

Another object of the present invention is to provide a process for the production of such catalysts and a method to use them.

The present invention solves the problem by the provision of a catalyst for the hydrogenation of unsaturated hydrocarbons, which catalyst is a supported nickel on silica ($SiO_2$) catalyst, has a nickel content of 40 to 85 weight-% (calculated as NiO), a silicon content of 15 to 60 weight-% (calculated as $SiO_2$), a titanium content of 0.5 to 5.0 weight-% (calculated as $TiO_2$), and does not contain more than 0.20 weight-% iron (calculated as Fe), wherein the catalyst has a monomodal Ni-crystallite size distribution with a mean crystallite size of the reduced catalyst of 1.5 to 3.5 nm, wherein the pore volume of pores with diameters from 1.7 to 300 nm is at least 0.60 ml/g and wherein the proportion of the pore volume of pores with a pore diameter of ≥10 nm is at least 55%.

Thus, the present invention solves its technical problem in particular by the provision of a supported catalyst which in a preferred embodiment has a nickel silicate phase, and which is characterised by a specific combination of its composition, pore volume distribution and crystallite size and distribution. Such a catalyst surprisingly provides, in contrast to conventional catalysts, a significantly higher activity and is of advantage due to its broad range of possible educts, in particular higher and lower molecular weight aromatic compounds.

Weight-% values given in the present teaching refer, if not otherwise stated, to the weight of the dry total catalyst. In the context of the present invention, the components of the catalysts are to be selected in an overall amount not to exceed 100 weight-%.

The invention provides a nickel on silica hydrogenation catalyst which is free of iron. In the context of the present invention, the term free of iron refers to a catalyst which does not contain substantial amounts of iron, in particular, does not contain more than 0.20 weight-% Fe (calculated as Fe). In a more preferred embodiment, the iron content of the iron-free catalyst is at maximum 0.1, most preferably at maximum 0.05 weight-% (calculated as Fe). In a particularly preferred embodiment, there is no detectable amount of iron in the catalyst, preferably no iron at all.

In a furthermore preferred embodiment, the sodium content of the catalyst is low, preferably less than 1 weight-%, most preferably less than 0.5 weight-%, in particular less than 0.2 weight-% most preferably less than 0.1 weight-% (calculated as $Na_2O$ and relative to ROI).

The pore volume is determined according to BJH (Barrett, Joyner and Halenda). For the determination of pore volumes and proportions thereof pores with a diameter from 1.7 to 300 nm are considered, if not otherwise indicated.

In a particularly preferred embodiment, the nickel content is from 40 to 80 weight-% (calculated as NiO on total catalyst weight).

In a furthermore preferred embodiment, the silicon content is from 15 to 40 weight-% (calculated as $SiO_2$ on total catalyst weight).

In a preferred embodiment of the present invention, the reduction level of the nickel in the present catalyst is expressed as ratio of metallic nickel to total nickel from 52 to 80%.

In a preferred embodiment of the present invention, the catalyst comprises, in particular, essentially consists, most preferred consists of nickel, silica, titanium and one or more of the elements, preferably in the form of its oxides, selected from the group consisting of aluminium, magnesium, zinc, chromium and zirconium. In a preferred embodiment, the catalyst comprises, preferably essentially consists, particularly consists, in addition to nickel and $SiO_2$, of aluminium and titanium, or their oxides.

In a most preferred embodiment of the present invention, the catalyst has an aluminium content of 2 to 10 weight-% (calculated as aluminium oxide, $Al_2O_3$, on total catalyst weight).

In a preferred embodiment of the present invention, the catalyst has a magnesium content of 0.1 to 3.0 weight-% (calculated as magnesium oxide, MgO, on total catalyst weight).

In a preferred embodiment of the present invention, the catalyst has a zinc content of 0.1 to 4.0 weight-% (calculated as zinc oxide, ZnO, on total catalyst weight).

In a preferred embodiment of the present invention, the catalyst has a chromium content of 0.1 to 0.3 weight-% (calculated as chromium oxide, $Cr_2O_3$, on total catalyst weight).

In a preferred embodiment of the present invention, the catalyst has a zirconium content of 0.1 to 3.0 weight-% (calculated as zirconium dioxide, $ZrO_2$, on total catalyst weight).

The catalyst has in a preferred embodiment, a compacted bulk density of at least 0.15, preferably at least 0.20, preferably at least 0.25 $kg/dm^3$, most preferably 0.25 to 0.35 $kg/dm^3$.

In a furthermore preferred embodiment, the BET surface area is at least 150, preferably at least 200, most preferably at least 250 $m^2/g$. In a furthermore preferred embodiment, the nickel metal surface area is at least 15, preferably at least 20, most preferably at least 23 $m^2/g$.

In a particularly preferred embodiment, the silicate support contains additionally one or more of the compounds selected from the group consisting of magnesium silicate, alumosilicate ($Al_2O_3,SiO_2$), $TiO_2$, nickel titanate, $ZrO_2$, nickel zirconate and ZnO. In a particularly preferred embodiment, the catalyst comprises, preferably essentially consists, particularly consists of 40 to 80 weight-% nickel (calculated as NiO), 15 to 40 weight-% silicon (calculated on $SiO_2$), 2 to 10 weight-% aluminium (calculated on $Al_2O_3$), 0.5 to 5.0 weight-% titanium (calculated as $TiO_2$) and 0.1 to 3.0 weight-% magnesium (calculated as MgO) and wherein the nickel of the catalyst has a reduction level of 52 to 80%, wherein the catalyst has a monomodal crystallite size distribution with a mean crystallite size of 1.5 to 3.5 nm of the reduced catalyst and wherein the pore volume of the catalyst of pores with a diameter from 1.7 to 300 nm is at least 0.60 ml/g and the proportion of the pores with a diameter of ≥10 nm is at least 55%.

Thus, the present invention solves its technical problem in particular by providing a nickel silicate phase based iron-free catalyst, which comprises, in particular essentially consists, particularly consists of (stated as element oxides) 40 to 85 weight-%, preferably 40 to 80 weight-%, NiO, 15 to 60 weight-%, preferably 15 to 40 weight-%, $SiO_2$, and 0.5 to 5 weight-% $TiO_2$, wherein at least one of the components selected from the group consisting of 2 to 10 weight-% $Al_2O_3$, 0.1 to 3.0 weight-% $ZrO_2$, 0.1 to 3.0 weight-% MgO, 0.1 to 4.0 weight-% ZnO and 0.1 to 0.3 weight-% $Cr_2O_3$ is contained therein, wherein the nickel of the catalyst has a reduction level of 52 to 80%, wherein the catalyst has a monomodal crystallite size distribution with a mean crystallite size of 1.5 to 3.5 nm of the reduced catalyst and wherein the pore volume of the catalyst of pores with a diameter from 1.7 to 300 nm is at least 0.60 ml/g and the proportion of the pores with a diameter of ≥10 nm is at least 55%. The present invention provides preferably such a nickel-containing silica-supported catalyst as defined above, wherein the silica support comprises one or more of the compounds selected from the group consisting of magnesium silicate, alumosilicate, $TiO_2$, nickel titanate, $ZrO_2$, nickel zirconate and ZnO, preferably wherein the nickel is supported on nickel silicate and alumosilicate, with $TiO_2$.

The invention furthermore foresees that the catalyst is, in a preferred embodiment, a catalyst in form of a powder, in particular for use in suspension or 2 0 slurry hydrogenation reactions. In a preferred embodiment of the present invention, the catalyst of the present invention is a powdered catalyst, whose pore volume is at least 0.68 ml/g. The particle size of the catalyst in powder form lies, in a further preferred embodiment, in the range from 2 to 50 μm, preferably from 2 to 22 μm, both preferably with a $d_{50}$ value of 4 to 15 μm, preferably 4 to 10 μm.

In a furthermore preferred embodiment, the catalyst of the present invention is a formed or moulded catalyst, which is in the present teaching also called a shaped catalyst, in particular for use in fixed or fluidised bed hydrogenation reactions. In a preferred embodiment, the shaped catalyst may be, for instance, in form of balls, spheres, tablets, pellets or extrudates.

In a preferred embodiment of the present invention, the catalyst is a shaped catalyst, wherein the proportion of the pore volume of pores with a pore diameter of ≥10 nm is at least 65%.

The present invention also provides a process for the preparation of a nickel on silica catalyst as defined herein, wherein the catalyst components are co-precipitated.

The present invention also provides a process for the preparation of a supported nickel on silica catalyst, which process comprises reacting a metal salt solution which comprises a nickel ion source and a titanium ion source, with a sodium waterglass solution at a pH from 8.0 to 9.5 at temperatures from 70° C. to 100° C., preferably 85° C. to 100° C., so as to co-precipitate a catalyst material and recovering the co-precipitated catalyst material to obtain a supported nickel on silica catalyst.

Any reactant utilised in the process of the invention should be substantially free of iron such that the resulting catalyst will not contain more than 0.20 weight-% of iron (calculated as Fe).

In a particularly preferred embodiment, the above identified solutions may be added simultaneously to the precipitation vessel, or one after the other.

In the context of the present invention, waterglass is meant to be a compound which is a $SiO_2$ source. Thus, in particular, waterglass in the context of the present invention is, for instance, a water soluble alkali silicate, $SiO_2$, mixtures of $SiO_2$ with alkali ions, alkali salts or oxides, hydrogen silicates, silicates, for instance, sodium silicate or the like.

In the context of the present invention, a sodium waterglass solution is taken to mean a, preferably aqueous, solution containing a mixture of waterglass and sodium, the latter for instance in form of NaOH or $Na_2CO_3$ (soda).

In a preferred embodiment of the present invention, the metal salt solution comprises $Ni^{2+}$ and $TiO^{2+}$, and one or more of $Al^{3+}$, $Cr^{3+}$, $Mg^{2+}$, $Zn^{2+}$ and $ZrO^{2+}$. In a preferred embodiment of the present invention, the metal salt solution is an acidic solution. In a preferred embodiment of the present invention, the metal salt solution is a nitrate solution.

In a preferred embodiment of the present invention, the sodium waterglass solution comprises one or more of $Al(OH)_4^-$, $TiO_2$, Zn and $ZrO_2$. In a furthermore preferred embodiment of the present invention, the sodium waterglass solution is an alkaline solution.

In a preferred embodiment of the present invention, the pH value is kept constant during the complete precipitation from 8.0 to 9.5. In a preferred embodiment of the present invention, the precipitation time and the subsequent stirring time each is from 1 hour to 3 hours, preferably each from 1.5 to 2.5 hours, particularly each 2 hours. In a particularly preferred embodiment, the precipitation is conducted under stirring. In a particularly preferred embodiment, the pH value achieved at or after completion of the precipitation is ≥9.0, preferably is ≥9.1 and is at maximum 9.5.

In a preferred embodiment, the invention provides a process as specified above, wherein after the precipitation, the obtained catalyst precipitate is filtered. In a preferred embodiment, the filtered catalyst precipitate, i.e. the filter cake obtained, is washed, preferably to a Na content of <0.2 weight-%, preferably <0.1 weight-%.

In a preferred embodiment of the present invention the, preferably washed, filter cake is subsequently dried, for instance by flash drying, spray drying or simple drying in conventional drying devices.

For the production of catalysts in powder form it is preferred to process the filter cake via spray drying.

In a particularly preferred embodiment, the dried catalyst may be further processed such as by granulation, preferably together with binder components and/or water. In a preferred embodiment, the granulated catalyst may be dried and calcined.

In a preferred embodiment of the present invention, the catalyst obtained according to the above process, in particular the dried catalyst, is calcined, for instance at temperatures from 120° C. to 350° C. In a furthermore preferred embodiment, the dried and calcined catalyst is reduced, preferably after a step of inerting the catalyst.

In a furthermore preferred embodiment, the dried catalyst is reduced, preferably in a fluidised bed, preferably in a stream of hydrogen, preferably at temperatures of 300° C. to 600° C., particularly 340° C. to 500° C. In another preferred embodiment, the reduction can, however, also be preformed in a rotary oven, a 3 0 cylinder rotary kiln or another suitable installation. In a furthermore preferred embodiment, the reduced catalyst is stabilised, for instance, in a nitrogen/air, $CO_2$/nitrogen/$O_2$ or nitrogen/$O_2$ atmosphere.

The powdered catalyst may, in a particularly preferred embodiment of the present invention, be produced by spray or flash drying of the catalyst precipitate and subsequent processing, in particular calcination and reduction.

In a further preferred embodiment of the present invention, the present catalyst can be produced in powdered form by shaping of the dried precipitation product, and subsequent reduction and stabilisation of the material with subsequent milling and screening of the reduced and stabilised catalyst.

The production of the shaped catalysts can be effected by known shaping processes. In accordance with the present invention, preferably extrusion and drop formation have been found particularly advantageous.

The present invention also provides a catalyst obtained or obtainable according to the above identified preparation processes.

The present invention also provides a process for the hydrogenation of unsaturated hydrocarbons, in particular aromatics, using the catalysts according to the present invention.

In a preferred embodiment of the present invention, the unsaturated hydrocarbons are provided, contacted with at least one catalyst according to the present teaching under suitable reaction conditions and hydrogenated hydrocarbons are obtained.

Temperatures and pressures suitable for conducting the present process for the hydrogenation of unsaturated hydrocarbons can be determined by the skilled person. In preferred embodiments, suitable reaction temperatures are from 70° C. to 350° C., preferably 250° C. to 350° C. In a furthermore preferred embodiment, partial hydrogen pressures can be used, for instance, from 1 to 250 bar, preferably 1 to 150 bar, preferably 30 to 140 bar. The hydrogenation process of the present invention may be carried out in fixed bed reactors, fluid bed reactors, slurry reactors, loop reactors or the like.

Examples of aromatics which preferably may be hydrogenated according to the present invention are kerosene, white oils, aromatic solvents or benzene.

The advantages of the invention will be illustrated by means of the following examples:

EXAMPLE 1

According to Invention 5 l of water are placed in a heatable precipitation vessel equipped with a stirrer and then titanium oxide is added in the form of an acidic titanyl sulphate solution. The solution is heated to a temperature of 80° C. to 90° C. with stirring. On attainment of the temperature, the parallel addition of a metal nitrate solution and an aqueous precipitant solution begins. In addition to nickel, the metal nitrate solution contains magnesium, aluminium and chromium. In addition to soda ($Na_2CO_3$), the precipitant solution contains a dissolved silicon dioxide compound. During the precipitation, the pH value is kept constant at 8 to 8.5. The precipitation time and further stirring time are each 2 hours.

The mole ratio of nickel to $SiO_2$, $Al_2O_3$, $Cr_2O_3$, MgO and $TiO_2$ is 1:0.5:0.04:0.0085:0.055:0.016.

After completion of the precipitation, the suspension is filtered and washed with alkali-free water until the $Na_2O$ content in the filter cake is <0.2% based on the residue on ignition (ROI) of the filter cake heat treated at 800° C.

After the filtration and washing, the filter cake obtained is again redispersed in water and then sprayed in a commercial spray dryer. The powder material obtained has a grain size of 6 μm. Next, the product is calcined for 2 hours at 350° C. and, after inerting, it is reduced in a current of hydrogen for 6 hours at 400° C. and stabilised in a $CO_2$/nitrogen stream with an oxygen content of 0.1 to 1 vol. % at temperatures below 80° C.

The reduced and stabilised catalyst contains approx. 55% nickel based on the total catalyst. It has a nickel reduction level, expressed by the ratio of metallic nickel to total nickel, of approx. 70%. The catalyst showed a monomodal Ni-crystallite size distribution. The mean nickel primary particle size (i.e. the mean crystallite size of the reduced catalyst) of the catalyst further reduced at 180° C. is about 3 nm. The XRD spectrum confirms the presence of a nickel silicate phase. The pore volume is 0.73 ml/g. The pore volume with pore diameters ≥10 nm is 0.42 ml/g.

EXAMPLE 2

According to Invention 15 l of water are placed in a heatable precipitation vessel and then kieselguhr as the $SiO_2$ component and solid $TiO_2$ (P 25, Degussa Co.) are added with stirring. This is followed by the addition of an aqueous sodium hydroxide solution (10%). After heating of the solution to 85° C., the metered addition of a combined metal nitrate solution, which contains nickel, aluminium, magnesium and chromium ions, begins. The mole ratio of nickel to $SiO_2$, $Al_2O_3$, MgO, $TiO_2$, $Cr_2O_3$ and ZnO is 1:0.4:0.038:0.05:0.016:0.004:0.006.

The precipitation time and subsequent stirring time at a mean temperature of 85° C. is approx. 2 hours for each. After the precipitation and subsequent stirring, the pH value is about 8.5. After the filtration and washing, the filter cake obtained is again redispersed and then sprayed in a commercial dryer. The powder material obtained has a mean grain size of 9 μm. The dry product is calcined at 350° C. in a stream of inert gas and then reduced in a stream of hydrogen in a fluidised bed at 350° C. for 2 hours. After the reduction, it is cooled in a stream of nitrogen, and stabilised in a nitrogen/air/$CO_2$ mixture with $O_2$ contents of 0.1-1 vol. %.

The reduced and stabilised catalyst contains approx. 58% nickel based on the total catalyst. It has a nickel reduction level, expressed by the ratio of metallic nickel to the total nickel, of approx. 55%. The catalyst showed a monomodal Ni-crystallite size distribution. The mean nickel primary particle size (i.e. the mean crystallite size of the reduced catalyst) of the catalyst further reduced at 180° C. is 2.7 nm. The XRD spectrum confirms the presence of a nickel silicate phase. The pore volume is 0.71 ml/g. The pore volume with pore diameters ≥10 nm is 0.40 ml/g.

EXAMPLE 3

According to Invention 10 l of water are placed in a heatable precipitation vessel and then the addition of a sodium aluminate solution (40 g $Al_2O_3$/l solution, 100 g NaOH/l) and waterglass solution (50 g $SiO_2$/l solution) is effected with stirring. After heating of the solution to 90° C. to 95° C., the metered addition of an aqueous nickel-, magnesium- and zirconium nitrate solution up to a pH value of 8.5 is started. The metal nitrate solution additionally contains $TiO_2$ in form of a titanyl sulphate solution. After attainment of the pH value of about 8.5, the parallel addition of the remaining nickel nitrate solution and an aqueous NaOH solution (10%) at temperatures of 90° C. to 95° C. begins. The precipitation time is 1 hour, the subsequent stirring time approx. 2 hours.

The mole ratio of nickel to $SiO_2$, $Al_2O_3$, MgO, $TiO_2$ and $ZrO_2$ is 1:0.39:0.038:0.036:0.016:0.01.

The further processing of the catalyst takes places as described in Example 1. The reduction is performed at a temperature of 420° C.

The reduced and stabilised catalyst contains approx. 60% nickel based on the total catalyst. It has a nickel reduction level of approx. 80%. The catalyst showed a monomodal Ni-crystallite size distribution. The mean nickel primary particle size (i.e. the mean crystallite size of the reduced catalyst) of the catalyst further reduced at 180° C. is 2.8 nm. The XRD spectrum confirms the presence of a nickel silicate phase. The pore volume is 0.77 ml/g. The pore volume with pore diameters ≥10 nm is 0.51 ml/g.

EXAMPLE 4

According to Invention 5 l of water and solid $TiO_2$ (P 25, Degussa Co.) are placed in a heatable precipitation vessel, then the suspension is heated with stirring to a temperature of 90° C. to 95° C. After attainment of the temperature, the parallel addition of a combined metal nitrate solution, which contains nickel, aluminium and magnesium in the form of the nitrates and an alkaline solution which is an aqueous solution of the precipitant soda and a dissolved $SiO_2$ compound, takes place. During the precipitation, the pH value is constantly adjusted to 8.0 to 8.3. The precipitation and subsequent stirring time are each approx. 2 hours.

The mole ratio of nickel to $SiO_2$, $Al_2O_3$, MgO and $TiO_2$ is 1:0.328:0.037:0.053:0.032.

After completion of the precipitation, the precipitation suspension is filtered and the filter cake washed with pure condensate until the $Na_2O$ content is <0.05% based on the filter cake weight taken. Next, the filter cake is dried at temperatures from 120° C. to 140° C. down to a residue on ignition (800° C.) of at least 70% and then calcined at 350° C. to 380° C. After completion of the calcination, the residue on ignition of the calcined material is at least 90%. The product obtained is now reduced in a suitable unit in a stream of hydrogen at temperatures from 420° C. to 430° C. for 10 hours and then stabilised at ambient temperature in an $O_2$ containing stream of nitrogen.

The reduced and stabilised catalyst is then finely ground in an inert gas mill under a protective atmosphere.

The finished powder catalyst has a nickel content of 60%, the reduction level is approx. 80%, and the mean crystallite size (i.e. the mean crystallite size of the reduced catalyst) of the catalyst further reduced at 180° C. is 3.1 nm. The catalyst showed a monomodal Ni-crystallite size distribution. The mean particle size of the catalyst is 15 μm, and the total pore volume is 0.70 ml/g, and the pore volume with pore diameters of ≥10 nm is 0.39 ml/g.

EXAMPLE 5

According to Invention 8 l of water and titanyl sulphate are placed in a precipitation vessel. After this, the addition of a sodium waterglass solution takes place with stirring within 30 mins. During the addition, the heating to the desired precipitation temperature of 90° C.

takes place. After attainment of the temperature, a pH value of approx. 8 is attained by addition of a combined nickel-, magnesium- and aluminium nitrate solution, and the mixture is then stirred for a further 30 mins. After this, the precipitation process is continued in that in parallel a sodium hydroxide solution (150 g/l) and the remaining metal nitrate solution are metered in. During the precipitation, the temperature remains constant at 90° C. The precipitation time and subsequent stirring time are each about 1 hour. The mole ratio of nickel to $SiO_2$, $Al_2O_3$, MgO and $TiO_2$ is 1:0.65:0.038:0.05:0.016.

The precipitation suspension is then filtered and the filter cake washed with very clean condensate. After this, the filter cake is again dispersed in water and made into drop form by the alginate method. After drying and calcination at temperatures of 130° C. and 400° C. respectively, the reduction of the moulded bodies is effected at a temperature of 420° C. in a stream of hydrogen. The stabilisation is performed as described in Example 1.

The finished catalyst has a nickel content of approx. 52%, the reduction level is approx. 70%, the mean crystallite size (i.e. the mean crystallite size of the reduced catalyst) of the catalyst further reduced at 180° C. is 3.2 nm and the catalyst has a particle size of 2-3 mm. The catalyst showed a monomodal Ni-crystallite size distribution. The pore volume is 0.70 ml/g, and the pore volume with pore diameters of ≥10 nm is 0.49 ml/g.

EXAMPLE 6

Comparative Example 10 l of water were placed in a precipitation vessel and then heated to 80° C. with stirring. After this, the parallel addition of a combined metal nitrate solution containing 1.4 kg nickel, 0.050 kg MgO, 0.050 kg $Al_2O_3$ and 0.0056 kg Fe and a soda/waterglass solution, which contains 2.9 kg soda and 0.345 kg $SiO_2$ was effected with stirring at a constant temperature of 80° C. The pH value during the precipitation was 7.5. The precipitation process was completed after 1 hour. After completion of the precipitation, the suspension was filtered and washed. The filter cake obtained was then dried at 110° C., finely ground and calcined at 350° C. The reduction of the catalyst educt material was effected in the fliud phase at a temperature of 400° C. After the stabilisation of the catalyst in a nitrogen/air mixture, the finished catalyst had the following composition:

60% nickel, 18% $SiO_2$, 2.7% $Al_2O_3$, 2% MgO and 0.3% $Fe_2O_3$.

The nickel reduction level in the catalyst was about 65%, and the nickel primary particle size about 3.5 nm. The pore volume (for pores with a diameter of 2 to 60 nm) is 0.35 ml/g. The pore volume is 0.41 ml/g, and the pore volume with pore diameters of ≥10 nm is 0.17 ml/g.

EXAMPLE 7

Comparative Example 10 l of water and the soda/waterglass solution used in Example 6 and being of the same composition were placed in the vessel and then heated to 80° C. After this, the addition of the combined metal nitrate solution, which contained 1.4 kg nickel, 0.050 kg $Al_2O_3$ and 0.0056 kg Fe was effected with stirring and a constant temperature of 80° C. After a precipitation time of 1 hour, the pH value of the precipitation suspension was 7.3. The precipitation slurry was filtered, washed and then sprayed in a commercial spray dryer. The mean particle size of the sprayed granules was approx. 10 μm. The calcination, reduction and stabilisation were effected in the fluidphase.

The finished catalyst had the following composition: 62% nickel, 19% $SiO_2$, 3% $Al_2O_3$ and 0.35% $Fe_2O_3$.

The nickel reduction level in the catalyst was 70%, and the nickel primary particle size 3.8 nm. The pore volume (for pores with a diameter of 2-60 nm) is 0.34 ml/g. The pore volume is 0.39 ml/g. The pore volume of the pores with pore diameters ≥10 nm is 0.13 ml/g.

EXAMPLE 8

Comparative Example

A dried and ground $Ni/SiO_2$ starting material with mean particle size of 10 μm and a bulk density of 0.7 kg/l was mixed with tylose as binder and then dispersed in a laboratory kneader with the addition of condensate water, nitric acid and silica sol solution. Based on the solids content of this kneader batch, the addition of tylose amounts to 2.5%. After a kneading time of 15 mins, the complete batch was shaped into 3 mm cylindric extrudates in a laboratory extruder with a cutting device. The moist extrudates obtained were further processed into spheres in a laboratory spheroniser (Caleva Co., Model 120, England). The sphere-shaped material obtained was then dried at 130° C.

The starting material was reduced at 400° C. in a stream of hydrogen as already described and stabilised under standard conditions.

The finished catalyst contains approx. 55% nickel and has a reduction degree of approx. 75%. The mean nickel crystallite size is 4.5 nm. The catalyst shows a broad particle size distribution with diameters of 2-4 mm. The pore volume is 0.30 ml/g, and the proportion of pores with pore diameters >10 nm is only 0.02 ml/g.

EXAMPLE 9

Comparative Catalysis

Table 1 below shows the composition of catalysts according to the invention and comparative catalyst used in the following comparative analysis

TABLE 1

| Example | wt.-% NiO | wt.-% SiO2 | wt.-% Al2O3 | wt.-% TiO2 | wt.-% ZrO2 | wt.-% MgO | wt.-% Cr2O3 | wt.-% ZnO | wt.-% Fe2O3 |
|---|---|---|---|---|---|---|---|---|---|
| 1 | 70 | 25 | 2 | 1 |  | 2 | 0.2 |  |  |
| 2 | 73 | 21.8 | 2.05 | 0.9 |  | 1.9 | 0.15 | 0.2 |  |
| 3 | 75 | 20.8 | 2 | 1 | 0.4 | 1.2 |  |  |  |
| 4 | 73 | 18.5 | 4 | 2.3 |  | 2.2 |  |  |  |
| 5 | 65 | 29.5 | 2.1 | 1.2 |  | 2.2 |  |  |  |
| 6 | 78 | 16 | 3.2 |  |  | 2.3 |  |  | 0.5 |
| 7 | 79 | 16.9 | 3.5 |  |  |  |  |  | 0.6 |
| 8 | 72 | 28 |  |  |  |  |  |  |  |
| 9 | 70 | 20 | 10 |  |  |  |  |  |  |

For the catalytic assessment, a commercial sphere-shaped nickel alumosilicate catalyst 9 with the following physico-chemical characteristics was also used:

TABLE 2

| Nickel content (wt. %) | 55 |
|---|---|
| Nickel reduction level (%) | 60 |
| Bulk density (kg/l) | 0.95 |
| Mean particle diameter (mm) | 2.5 |
| Particle diameter range (mm) | 1.6-4.7 |
| Pore volume (ml/g) | 0.27 |
| Pore volume > 10 nm | 0.19 |
| Nickel crystallite size (nm) | 5.1 |

Catalyst 5 produced according to the invention and the comparative catalysts 8 and 9 were used for the catalytic assessment of the hydrogenation of aromatics in a fixed bed process.

For the catalytic characterisation of the Ni supported catalysts, the aromatics hydrogenation of kerosene using an integral flow reactor (internal diameter: 25 mm) was used. The incorporated catalyst volume was 50 ml. The 50 ml of catalyst were in each case incorporated in 10 portions with 10 portions of SiC in a volume ratio of 1:1. Before the catalytic reaction, the catalysts were reactivated in a stream of hydrogen (50 l/hr) over a period of 4 hours at 250° C. As feed, a kerosene with an aromatics content of 18 weight-% and a sulphur content of 1.1 ppm was used. The other experimental conditions were:
Reaction pressure: 30 bar
Reaction temperature: 85° C., reaction time: 40 hours
  100° C., reaction time: 80 hours
LHSV: 1.3
Gas—product ratio: 400 l $H_2$/l kerosene
  The results are shown in Table 3.

TABLE 3

| Catalyst | Reaction temperature: 85° C. ppm aromatics | Reaction temperature: 100° C. ppm aromatics |
|---|---|---|
| Example 5 according to invention | 1490 | 139 |
| comparative example 8 | 2640 | 259 |
| comparative example 9 | 3105 | 298 |

A comparison of the catalytic measurement results shows the superiority of the catalysts according to the invention: the degree of hydrogenation or degradation of the aromatics up to the ppm range is significantly greater with the catalyst according to the invention than with the conventional catalysts.

The catalytic characterisation of the powder catalysts was carried out using a stirred autoclave from the Autoclave Engineers Co.: 210 g of a resin (mean molecular weight: 2750 g), 90 g of Shellsol and 1.8 g of catalyst were transferred into the autoclave and after inerting the autoclave was charged with hydrogen to a pressure of 4 bar. Next, the autoclave content was heated to a temperature of 270° C. After attainment of this temperature, the reaction pressure of 90 bar was established and the stirrer then set into operation. The stirring speed was 2200 rates per minute. The hydrogen consumption under constant pressure as a function of the reaction time was measured. The mean rate in 1 $H_2$/hr $g_{catalyst}$ calculated from the hydrogen consumption between the 10th and 30th minute after the start of reaction served as the measure of activity.

The results of the catalytic measurement results are shown in Table 4.

TABLE 4

| Catalyst | Hydrogenation activity in 1 $H_2$/hr g |
|---|---|
| Example 1 according to invention | 15.6 |
| Example 2 according to invention | 16.1 |
| Example 3 according to invention | 15.2 |
| Example 4 according to invention | 16.0 |
| Example 6 (comparative example) | 12.8 |
| Example 7 (comparative example) | 13.3 |

The data in Table 4 clearly shows that the catalysts according to the invention have a higher hydrogenation activity than the comparative catalysts.

The invention claimed is:

1. A process for the preparation of a supported nickel on silica catalyst which catalyst has a nickel content of 40 to 85 weight-% (calculated as NiO), a silicon content of 15 to 60 weight-% (calculated as $SiO_2$), a titanium content of 0.5 to 5.0 weight-% (calculated as $TiO_2$), and does not contain more than 0.20 weight-% iron (calculated as Fe), wherein the catalyst has a monomodal Ni-crystallite size distribution with a mean crystallite size of the reduced catalyst of 1.5 to 3.5 nm, a pore volume of at least 0.60 ml/g and wherein the proportion of the pore volume of pores with a pore diameter of ≥10 nm is at least 55%;
  wherein the process comprises reacting a metal salt solution which comprises a nickel ion source and a titanium ion source and which is substantially free of iron with a sodium waterglass solution, which waterglass is a $SiO_2$ source, at a pH from 8 to 9.5 and at a temperature from 70° C. to 100° C., so as to co-precipitate a catalyst material and recovering the co-precipitated catalyst material to obtain a supported nickel on silica catalyst, and optionally drying, calcining and reducing.

2. A process as claimed in claim 1, wherein the metal salt solution comprises $Ni^{2+}$ and $TiO^{2+}$, and one or more ions selected from $Al^{3+}$, $Cr^{3+}$, $Mg^{2+}$, $Zn^{2+}$, and $ZrO^{2+}$.

3. A process as claimed in claim 1, wherein the sodium waterglass solution comprises $Al(OH)_4^-$, $TiO_2$, ZnO or $ZrO_2$.

4. A process as claimed in claim 1, wherein the reduction level of nickel in the catalyst is from 52 to 80%.

5. A process as claimed in claim 1, wherein the catalyst has a zinc content of 0.1 to 4.0 weight-% (calculated as ZnO).

6. A process as claimed in claim 1, wherein the catalyst has a chromium content of 0.1 to 0.3 weight-% (calculated as $Cr_2O_3$).

7. A process as claimed in claim 1, wherein the catalyst has a zirconium content of 0.1 to 3.0 weight-% (calculated as $ZrO_2$).

8. A process as claimed in claim 1, wherein the catalyst is a powdered catalyst whose pore volume is at least 0.68 ml/g, or which is a shaped catalyst wherein the proportion of the pore volume of pores with a pore diameter ≥10 nm is at least 65%.

9. A process as claimed in claim 1, wherein the support contains one or more of the compounds selected from the group consisting of magnesium silicate, alumosilicate, $TiO_2$, nickel titanate, zirconium dioxide, nickel zirconate and ZnO.

10. A process as claimed in claim 1, wherein the catalyst has an aluminum content of 2 to 10 weight-% (calculated as $Al_2O_3$).

11. A process as claimed in claim 1, wherein the catalyst has a magnesium content of 0.1 to 3.0 weight-% (calculated as MgO).

12. A process for the hydrogenation of unsaturated hydrocarbons, wherein the unsaturated hydrocarbons are provided, contacted with at a catalyst under reaction conditions and hydrogenated hydrocarbons are obtained, wherein the catalyst is a supported nickel on silica catalyst which catalyst has a nickel content of 40 to 85 weight-% (calculated as NiO), a silicon content of 15 to 60 weight-% (calculated as $SiO_2$), a titanium content of 0.5 to 5.0 weight-% (calculated as $TiO_2$), and does not contain more than 0.20 weight-% iron (calculated as Fe), wherein the catalyst has a monomodal Ni-crystallite size distribution with a mean crystallite size of the reduced catalyst of 1.5 to 3.5 nm, a pore volume of at least 0.60 ml/g and wherein the proportion of the pore volume of pores with a pore diameter of ≥10 nm is at least 55%.

13. A process for the hydrogenation of unsaturated hydrocarbons according to claim 12, wherein the unsaturated hydrocarbons are aromatic compounds.

* * * * *